United States Patent [19]

Shaw et al.

[11] 4,322,164

[45] Mar. 30, 1982

[54] STERILIZABLE, DISPOSABLE OPTICAL SCATTERING REFERENCE MEDIUM AND CONTAINER ASSEMBLY

[75] Inventors: Robert F. Shaw, Portola Valley; John M. Sperinde, San Jose, both of Calif.

[73] Assignee: Oximetrix, Inc., Mountain View, Calif.

[21] Appl. No.: 52,065

[22] Filed: Jun. 25, 1979

Related U.S. Application Data

[63] Continuation of Ser. No. 733,280, Oct. 18, 1976, abandoned.

[51] Int. Cl.³ .............................................. G01J 1/02
[52] U.S. Cl. .................................... 356/243; 356/41; 356/42
[58] Field of Search ............... 128/6, 632, 634, 633, 128/; 250/227, 252; 350/105, 96.2-96, 22; 362/32; 356/665, 666, 39-42, 243

[56] References Cited

U.S. PATENT DOCUMENTS

| | | | |
|---|---|---|---|
| 3,029,682 | 4/1962 | Wood | 356/41 |
| 3,234,846 | 2/1966 | Cropper et al. | 356/243 X |
| 3,296,922 | 1/1967 | Goldberg | 356/40 |
| 3,520,626 | 7/1970 | Hach | 356/42 X |
| 3,638,640 | 2/1972 | Shaw | 128/633 |
| 3,683,167 | 8/1972 | Rishton | 350/96.2 X |
| 3,706,499 | 12/1972 | Rapoza et al. | 356/414 |
| 3,764,364 | 10/1973 | Seiner | 356/243 X |
| 3,807,390 | 4/1974 | Ostrowski | 128/634 |
| 3,922,064 | 11/1975 | Clark et al. | 350/96.22 X |
| 3,947,088 | 3/1976 | French | 250/227 X |
| 3,947,122 | 3/1976 | Walker | 356/41 |
| 4,033,330 | 7/1977 | Willis et al. | 356/42 X |
| 4,082,946 | 4/1970 | Heine et al. | 128/6 X |

OTHER PUBLICATIONS

Erb, W. "Requirements for Reflection Standards and the Measurement of their Relfection Values", Applied Optics. V. 14#2, Feb. 1975 pp. 493-499.
Electronics, Aug. 5, 1976 pp. 97-99.

Primary Examiner—Robert W. Michell
Assistant Examiner—Francis J. Jaworski
Attorney, Agent, or Firm—Lyon & Lyon

[57] ABSTRACT

An optical scattering reference medium is formed of a plurality of scattering particles substantially uniformly dispersed in a substantially compliant, non-compressable transparent solid medium which is selectively positionable against the distal end of an optical catheter for use therewith within a sterilizable disposable package for performing repeatable photometric measurements to standardize the performance of the photometric measuring instrument.

13 Claims, 2 Drawing Figures

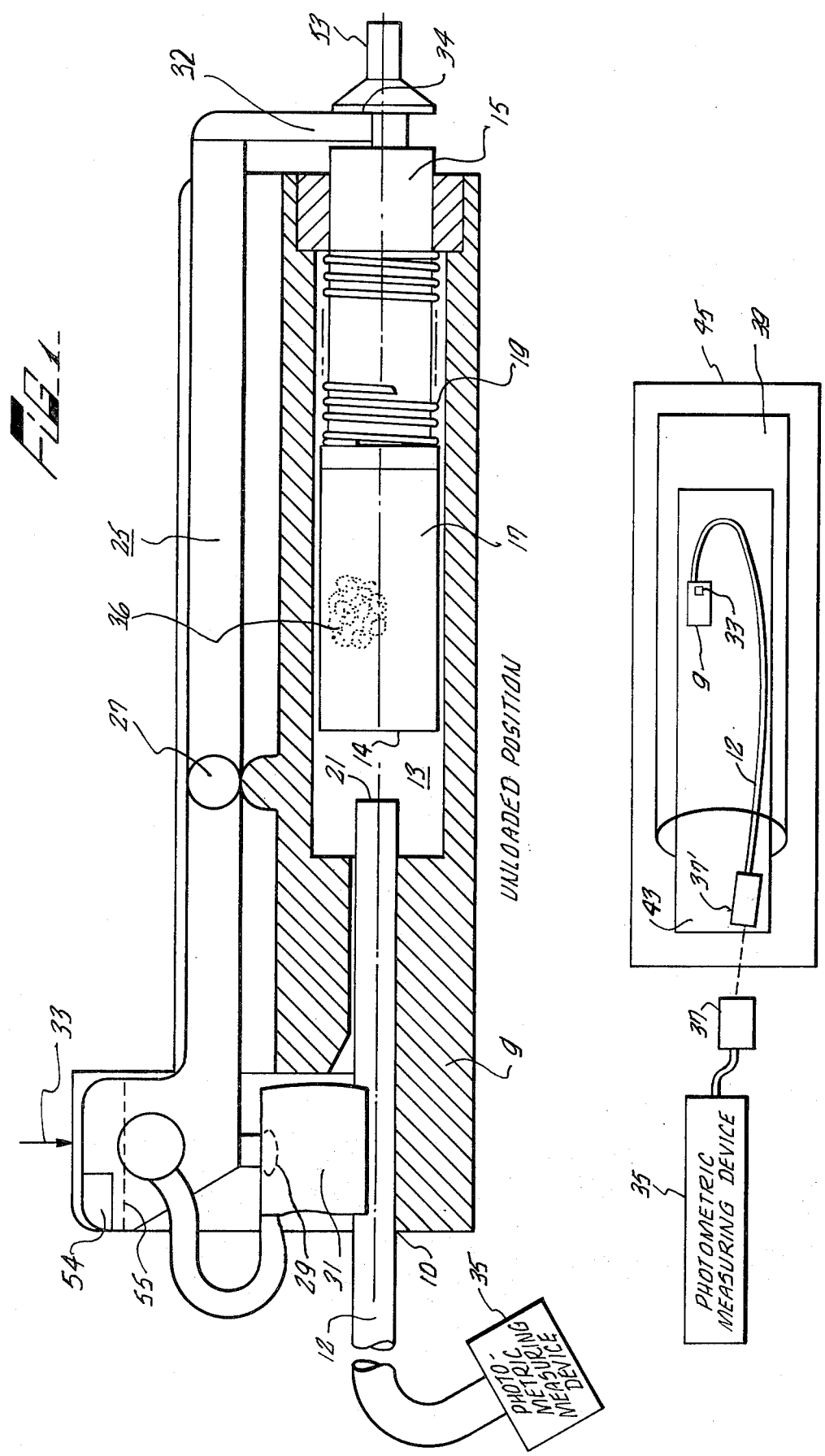

STERILIZABLE, DISPOSABLE OPTICAL SCATTERING REFERENCE MEDIUM AND CONTAINER ASSEMBLY

This is a continuation of application Ser. No. 733,280, filed Oct. 18, 1976, now abandoned.

RELATED APPLICATIONS

The subject matter of this application relates to the subject matter of U.S. Pat. No. 4,114,604, entitled Improved Catheter Oximeter Apparatus, filed Oct. 18, 1976, and to the subject matter of pending application Ser. No. 733,279, now abandoned, entitled Improved Optical Catheter Not Requiring Individual Calibrations, filed Oct. 18, 1976, the disclosures of which are incorporated herein by reference.

BACKGROUND OF THE INVENTION

In determining the unknown concentration of known substances by photometric measurements, two techniques are available to relate the actual light intensities received from the sample under test to the unknown concentrations of the substances being quantified in the sample under test.

One of these techniques is the "Calibration Technique". In this technique, the actual light intensities received after transmission through or reflectance from a sample having known concentrations of the substances being quantified are utilized to produce a "calibration curve". Thereafter, actual light intensity measurements obtained from a sample having unknown concentrations of the substances being quantified can then be utilized relative to the calibration curve to quantify the concentrations (S) of such substances.

The "calibration technique" has been commonly used in catheter oximetry. An optical catheter may be inserted into the blood stream of a patient and the blood oxygenation of the patient varied by having the patient breathe mixtures enriched with or depleted of oxygen. While light intensity measurements are made, blood samples are withdrawn, usually through the catheter. The oxygen saturation of these blood samples are then independently measured on a separate instrument, often in a central laboratory. After these measurements have been completed, oxygen saturation can be determined, by comparison of actual light intensities measurements relative to the calibration curve which was derived from the two known conditions of oxygen saturation. Such a calibration curve may be introduced electronically into the catheter oximeter system so that automatic computed oxygen saturation may be displayed.

This technique has several disadvantages. First, blood oxygen saturation levels are imposed upon the patient which may be deleterious to his health. Second, there is an undesirable delay between the time of catheter placement and the time at which oxygen saturation measurements utilizing the catheter oximeter can be obtained. Third, changes in blood oxygen level occur continuously and often very rapidly, making it difficult to be certain that the blood sample and the actual light intensity reading are truly correlated.

In order to eliminate the first and second disadvantages referred to above, efforts have been made to precalibrate the catheters in blood samples or suspensions of other materials such as milk of magnesia combined with dyes or filters which are believed to produce light intensity measurements equivalent to blood of known oxygen saturations. (See Taylor et al., *Journal of the American Medical Association*, Aug. 14, 1972, page 669; Frommer et al., *The American Journal of Cardiology*, May 1965, page 672; Gamble et al., *Circulation*, March 1965, page 331).

These calibration techniques have many disadvantages. In all of them, sterility of the catheter and of the liquid sample is difficult to maintain. In all of them, the materials in suspension (e.g. red blood cells or magnesium oxide particles) tend to be non-uniform and tend to settle. If settling is prevented by stirring the samples, the flow patterns are highly variable at different measurement sites within the sample and the flow profile and the resultant orientation of red blood cells or chemical particles is usually not similar to that found in vivo. Lastly, manipulations utilizing liquid suspensions and dyes or filters to simulate the changes produced in actually measured light intensities measured as a function of changes in blood oxygen saturation have not been satisfactory.

Another technique commonly used to relate actual light intensity measurements to the concentration of known substrates under test may be referred to as the "Differential Spectrophotometric Technique". In this technique, "Reference" light intensity measurements $I_o$ (either transmission or reflectance) are made on a material having optical properties similar to the material to be tested but lacking the specific substances to be quantified. Thereafter, actual light-intensity measurements $I_s$ may be made on the material under test including the substances to be quantified, and these light intensity measurements $I_s$ are referenced against such "Reference" light intensity measurements $I_o$ previously obtained. The substance of interest can then be quantified from the known relationship between the concentrations of the substances and the actual light intensity measurements $I_s$ normalized to the reference light intensity measurements $I_o$.

SUMMARY OF THE INVENTION

In accordance with the present invention, a solid reference element having optical properties similar to those of blood, is used to provide reference light intensity measurements $I_o$ for normalizing actual light intensity measurements $I_s$ in the differential spectrophotometric technique. The reference element is contained within an apparatus which is disposable and sterilizable and which automatically couples the reference element to the distal tip of an optical catheter in a convenient, repeatable fashion and within a sterile environment. This apparatus including the reference element and an optical catheter are assembled within a dual-envelope sterilizable package which permits the catheter oximeter system to be standardized prior to use and in which the catheter can remain in sterile condition until its use is desired.

DESCRIPTION OF THE DRAWING

FIG. 1 is a cross-sectional view of the reference element contained within a housing which receives the end of an optical catheter to be calibrated; and FIG. 2 is a plan view showing enclosures disposed about the optical catheter and reference element illustrated in FIG. 1.

DESCRIPTION OF THE PREFERRED EMBODIMENT

Referring now to FIG. 1, there is shown a body 9 of a housing which includes an aperture 10 at one end thereof for receiving an optical catheter 12, and having a longitudinal bore 13 therein aligned with the aperture 10. A plunger element 15 is disposed within the bore 13 and has attached thereto a reference element 17 which is described in detail hereinafter. The plunger element 15 and the reference element 17 attached thereto are disposed to move longitudinally within the bore 13 in a direction toward the end 21 of catheter 12 that is disposed within the bore 13. A spring 19 is positioned between the end of the body 9 and the plunger element 15 to urge the reference element 17 in a direction toward the end 21 of catheter 12. The plunger element 15 is restrained from moving toward the end 21 of catheter 12 under the influence of spring 19 by a manually-operable latch mechanism 25 which is pivoted for movement about an axis 27 and which has a clamp block 31 attached at the other end of latch mechanism 25.

In operation, the optical catheter 12 is positioned within the body 9, as shown in FIG. 1, and is held lightly clamped in position by the clamp block 31. In order to perform the reference photometric measurement, the reference element 17 must be brought into intimate optical contact with the end 21 of optical catheter 12. This is accomplished by manually depressing region 33 of latch mechanism 25 which simultaneously tips the end 32 of the latch mechanism 25 out of engagement with a detent 34 in the plunger element 15 to allow the reference element 17 to be urged into intimate optical contact with the distal end 21 of the optical catheter 12 by the spring 19.

The movement of region 33 of latch mechanism 25 also causes step 54 of latch mechanism 25 to engage a retaining catch 55 attached to the body 9 for maintaining force on the resilient clamp block 31 to securely hold the catheter 12 in place against the longitudinal force exerted thereon by spring 19, the plunger element 15 and reference element 17. A suitable marking may be carried on surface 53 to indicate when the plunger element 15 is in the proper axial position for the standardization process. Thus, the apparatus illustrated in FIG. 1 may be manually actuated to establish the requisite conditions for standardizing the performance of an associated photometric measuring device 35 which may be attached to the proximal end of the catheter 12. In practice, optical coupling of a catheter 12 to a photometric measuring device 35 may be accomplished through optical connectors 37 and 37', as shown in FIG. 2 and as more fully described in Application Ser. No. 733,279, now abandoned.

After the reference photometric measurements are performed and the performance characteristics of the photometric measuring system are standardized, the catheter is ready to use and may be withdrawn from the aperture 10 in the body 9. This is accomplished by pulling the catheter 12 outwardly from the body 9, causing clamp block 31, which is provided with a recess which resiliently engages extension 29, to move sufficiently to permit removal of the catheter 12. The catheter 12, in cooperation with the photometric measuring device 35 is then ready for use in a patient.

The reference element 17 shown in FIG. 1 may be formed by uniformly dispersing particles 36 into a liquid medium which may be cured to form a substantially solid mass. The particles 36 should have dimensions within the range 0.02 to 20 microns, and should be uniformly dispersed within the solid mass. The solid mass should be substantially transparent, compliant at the surface 14 and noncompressible. The concentration of particles within the mass should be the same from mass to mass for all reference elements 17 in a population of reference elements, and should be of a magnitude to produce signals during reference photometric measurements made therewith that are of the same order of magnitude as signals produced during measurement of the materials to be tested.

For reference elements 17 that are to be used with optical catheters which aid in measuring the oxygen saturation of blood under test, the particles 36 may be titanium dioxide in a range of particle concentrations between about 0.001% and 1.0% by weight. Other light-scattering particles such as oxides, sulphates and carbonates of magnesium, barium and calcium, or the like, may also be used. Silicone resins which cure to a substantially transparent, compliant and incompressible solid mass are suitable for use as the vehicle to retain the particles in substantially uniform dispersion. The mass of the reference element 17 should exhibit compliant characteristics at least at the surface 13 to assure intimate optical engagement of the surface 14 of the reference element 17 with the ends or apertures of the optical fibers that are exposed at the distal tip 21 at the catheter 12. The incompressible characteristic of the mass is desirable to prevent changes in concentration of the uniformly dispersed particles 36 within the mass. Also, the substantial transparency of the mass is desirable to ensure that the intensity of light back-scattered from the uniformly-dispersed particles 36 is not differentially influenced by photometric signals of different wavebands. The transparency desired for the mass of reference elements 17 that are to be used with optical catheters which aid in measuring oxygen saturation of blood under test should be about the order of magnitude of optical transparency as that of blood under test.

Referring now to FIG. 2, there is shown a pictorial diagram of the catheter 12 having its distal end 21 disposed within the body 9 of the assembly shown in FIG. 1, and having a proximal end which is attached to one section 37' of an optical coupler. This assembly is disposed within a flexible and transparent first envelope 39 which encloses and enseals the optical catheter 12 except for the optical coupler 37'. The entire assembly including the envelope 39 and the optical coupler 37' and a supporting tray 43 therefor is enclosed within a second envelope 45 which is completely sealed to provide an impervious barrier to microorganisms. The envelopes 39 and 45 may be formed of a suitable material such as polyethylene film, or the like. This entire assembly may be sterilized by standard techniques such as irradiation or ethylene oxide gas sterilization.

To prepare a catheter 12 for use, the outer envelope 45 is removed to expose the optical coupler 37'. Without disturbing the bacteriological sterility of the rest of the assembly, the optical coupler 37' is attached to its mating optical coupler 37 which forms a part of the photometric measuring device 35. To initiate the reference measurement procedure, latch mechanism 25 is depressed in the region 33 by applying force thereto through the envelope 39.

After the requisite standardization procedures for device 35 catheter 12 are completed, the catheter 12 and photometric measuring system including the catheter 12 and device 35 are ready for use. The catheter 12 may remain within the envelope 39 until it is required to make a measurement, at which time the catheter 12 may be aseptically removed from the envelope 39. The catheter 12 may then be pulled from the body 9, as described above, and the distal end 21 of the catheter 12 may be introduced into the material under test.

We claim:

1. Apparatus for providing a calibration reference for use with a light guide that cooperates with a photometric measuring device in making light intensity measurements at a number of selected wavebands, the apparatus comprising (a) a plurality of light-scattering particles substantially uniformly dispersed throughout a solid medium that has a substantially incompressible body which is sufficiently compliant at its surface for intimate physical contact with the end of the light guide; and (b) means for urging and maintaining intimate physical contact between the end of the light guide and the compliant surface.

2. Apparatus as in claim 1 wherein said medium is sufficiently transparent at the selected wavebands of a photometric measuring device to transmit light that is scattered from within the body to the compliant surface in contact with the light guide.

3. Apparatus as in claim 1 for providing a light-scattering reference means for operation with a photometric measuring device which measures oxygen saturation of blood, wherein the light-scattering particles have dimensions within the range of from about 0.02 to 20 microns.

4. Apparatus as in claim 1 for providing a light-scattering reference means for operation with a photometric measuring device which measures oxygen saturation of blood, wherein the density of light-scattering particles within said medium ranges from about 0.001% to 1.0% by weight.

5. Apparatus as in claim 1 wherein said light-scattering particles are materials selected from the group consisting of oxides, carbonates, sulphates of titanium, magnesium, calcium and barium.

6. An assembly adapted for use with an optical catheter which has a light guide and which is capable of cooperating with a photometric measuring device in making light intensity measurements comprising:
   clamp means disposed to receive the optical catheter near an end of the catheter and to restrain the optical catheter against movement in a direction substantially along the length thereof,
   resilient means disposed to urge a reference surface into intimate physical engagement with the end of the light guide of the optical catheter restrained by the clamp means for providing a medium for reference measurements at the end of the light guide, and
   actuating means supported on said clamp means for causing said clamp means to restrain the optical catheter received by said clamp means and to cause said resilient means to urge said reference surface into engagement with the end of the optical catheter received by said clamp means in response to manual manipulation of said actuating means.

7. Apparatus for providing a calibration reference for use with a light guide that cooperates with a photometric measuring device in making light intensity measurements at a number of selected wavebands, the apparatus comprising (a) a plurality of light-scattering particles substantially uniformly dispersed throughout a solid medium that has a substantially imcompressible body which is sufficiently compliant at its surface for intimate physical contact with the end of the light guide; and (b) means for urging and maintaining intimate physical contact between the end of the light guide and the compliant surface, said means for urging and maintaining comprising (i) clamp means disposed to restrain said light guide against movement in a direction substantially along the length of the light guide; and (ii) resilient means disposed to urge said compliant surface into intimate physical engagement with the end of said light guide when the light guide is clamped by said clamp means, said resilient means urging with a force which is substantially constant and reproducible in said assembly and in each assembly within a population of such assemblies.

8. An assembly for use with an optical catheter which has a light guide and which is capable of cooperating with a photometric measuring device in making light intensity measurements comprising
   apparatus for providing a reference means for operation with a photometric measuring device which operates on radiation at selected wavebands, the apparatus including a plurality of light-scattering particles dispersed within a solid medium having a substantially incompressible body,
   clamp means disposed to receive the optical catheter near an end of the catheter and to restrain the optical catheter against movement in a direction substantially along the length of the catheter,
   resilient means disposed to urge a reference surface of said reference means into intimate physical engagement with the end of the light guide of the optical catheter restrained by said clamp means for providing a medium for reference measurements at the end of the light guide,
   housing means disposed to receive the optical catheter near one end of the catheter and to support said clamp means near said one end to selectively engage the optical catheter received by the housing means,
   said housing means supporting said resilient means for movement relative thereto to selectively engage said reference surface with the end of the optical catheter received by said housing means, and
   actuating means supported on said housing means for actuating said clamp means to restrain the optical catheter received by said housing means and to actuate said resilient means to resiliently urge said reference surface into intimate physical engagement with the end of the optical catheter received by said housing means in response to manual manipulation of said actuating means.

9. In combination with the assembly of claim 8:
   an optical catheter having a light guide extending therethrough from a distal end to a proximal end thereof, said optical catheter having its distal end received by the assembly and having a proximal end which forms an optical coupler;
   inner enclosure means disposed about the assembly having the optical catheter to form an enclosure thereabout with a region thereof having a flexible portion adjacent the actuating means to facilitate manual manipulation of the actuating means supported on said housing means, the inner enclosure means having an opening through which the proximal end and optical coupler formed thereon protrude; and outer enclosure means disposed about the inner enclosure means having the optical coupler and forming an enclosure thereabout.

10. An apparatus for providing an optical reference element adapted for use with a light guide comprising, clamp means disposed to restrain said light guide against movement in a direction substantially along the length thereof, resilient means disposed to urge the optical reference element into intimate physical engagement with the end of said light guide when said light guide is restrained by the clamp means, and actuating means connected to said clamp means for causing said clamp means to restrain said light guide and for causing said resilient means to urge said reference element into intimate physical engagement with said light guide in response to manual manipulation of said actuating means.

11. Apparatus for providing a calibration reference for use with a light guide that cooperates with a photometric measuring device in making light intensity measurements at a number of selected wavebands, the apparatus comprising (a) a plurality of light-scattering particles substantially uniformly dispersed throughout a solid medium that has a substantially incompressible body which is sufficiently compliant at its surface for intimate physical contact with the end of the light guide; and (b) means for urging and maintaining intimate physical contact between the end of the light guide and the compliant surface, said means for urging and maintaining comprising (i) clamp means adapted to restrain the light guide against movement in a direction substantially along the length thereof, and (ii) resilient means adapted to urge the compliant surface of said incompressible body against the end of the light guide to achieve intimate physical engagement therewith.

12. Apparatus for providing a calibration reference for use with a light guide that cooperates with a photometric measuring device in making light intensity measurements at a number of selected wavebands, the apparatus comprising (a) a plurality of light-scattering particles substantially uniformly dispersed throughout a solid medium that has a substantially incompressible body which is sufficiently compliant at its surface for intimate physical contact with the end of the light guide; and (b) means for urging and maintaining intimate physical contact between the end of the light guide and the compliant surface, said means for urging and maintaining comprising (i) clamp means disposed to restrain said light guide against movement in a direction substantially along the length of the light guide; and (ii) resilient means disposed to urge said compliant surface into intimate physical engagement with the end of said light guide when the light guide is clamped by said clamp means, said resilient means urging with a force which is substantially constant and reproducible in said assembly and in each assembly within a population of such assemblies; and (c) actuating means connected to said clamp means for causing said resilient means to urge said compliant surface of said incompressible body into intimate physical engagement with the end of the light guide in response to manual manipulation of said actuating means.

13. A method for calibrating a photometric measuring device having a light guide comprising the steps of:

(a) selecting a calibration reference comprising a plurality of light-scattering particles substantially uniformly dispersed throughout a solid medium that has a substantially incompressible body which is sufficiently compliant at its surface for intimate physical contact with the end of the light guide; and (b) urging and maintaining intimate physical contact between the end of the light guide and the compliant surface during calibration of the photometric measuring device.

* * * * *